(12) United States Patent
Tanisaka et al.

(10) Patent No.: US 10,668,083 B2
(45) Date of Patent: Jun. 2, 2020

(54) PHARMACEUTICAL COMPOSITION

(71) Applicant: FUJIFILM CORPORATION, Minato-ku, Tokyo (JP)

(72) Inventors: Hiroki Tanisaka, Kanagawa (JP); Kyoko Senga, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 11 days.

(21) Appl. No.: 16/181,248

(22) Filed: Nov. 5, 2018

(65) Prior Publication Data

US 2019/0070195 A1 Mar. 7, 2019

Related U.S. Application Data

(63) Continuation of application No. PCT/JP2017/018739, filed on May 18, 2017.

(30) Foreign Application Priority Data

May 31, 2016 (JP) .................. 2016-109268

(51) Int. Cl.
| | |
|---|---|
| A61K 31/565 | (2006.01) |
| A61K 47/10 | (2017.01) |
| A61K 47/14 | (2017.01) |
| A61K 9/08 | (2006.01) |
| A61P 5/32 | (2006.01) |
| A61K 9/00 | (2006.01) |
| A61K 47/44 | (2017.01) |
| A61P 35/00 | (2006.01) |

(52) U.S. Cl.
CPC .......... *A61K 31/565* (2013.01); *A61K 9/0019* (2013.01); *A61K 9/08* (2013.01); *A61K 47/10* (2013.01); *A61K 47/14* (2013.01); *A61K 47/44* (2013.01); *A61P 5/32* (2018.01); *A61P 35/00* (2018.01)

(58) Field of Classification Search
CPC ...... A61K 31/565; A61K 47/10; A61K 47/14; A61K 47/44; A61P 5/32
See application file for complete search history.

(56) References Cited

U.S. PATENT DOCUMENTS

| | | |
|---|---|---|
| 2001/0020016 A1 | 9/2001 | Evans et al. |
| 2009/0227549 A1 | 9/2009 | Palepu |
| 2013/0267489 A1 | 10/2013 | Teja et al. |
| 2015/0105357 A1 | 4/2015 | Lu et al. |
| 2016/0213682 A1* | 7/2016 | Ahmed ................ A61K 9/0019 |
| 2017/0027958 A1* | 2/2017 | Patel .................. A61K 31/4439 |

FOREIGN PATENT DOCUMENTS

| | | |
|---|---|---|
| EP | 2832349 A1 | 2/2015 |
| JP | 2003-519659 A | 6/2003 |
| JP | 2004-534093 A | 11/2004 |
| JP | 3713237 B2 | 11/2005 |
| JP | 2009-509942 A | 3/2009 |
| JP | 2011-514349 A | 5/2011 |
| JP | 2015-511606 A | 4/2015 |
| JP | 2015-134724 A | 7/2015 |
| WO | 2007/033434 A1 | 3/2007 |
| WO | 2015/033302 A2 | 3/2015 |

OTHER PUBLICATIONS

Extended European Search Report dated Apr. 12, 2019, issued in corresponding EP Patent Application No. 17806404.4.
International Search Report issued in International Application No. PCT/JP2017/018739 dated Jun. 13, 2017.
Written Opinion of the ISA issued in International Application No. PCT/JP2017/018739 dated Jun. 13, 2017.
Howell, Anthony et al., "Fulvestrant Revisited: Efficacy and Safety of the 500-mg Dose," Clinical Breast Cancer, vol. 11, No. 4, Aug. 2011, pp. 204-210 ISSN:1526-8209.

* cited by examiner

*Primary Examiner* — Barbara P Badio

(74) *Attorney, Agent, or Firm* — Solaris Intellectual Property Group, PLLC

(57) ABSTRACT

Provided is a pharmaceutical composition which contains fulvestrant in an amount of 4.5% by mass to 10.0% by mass with respect to the entire mass of the pharmaceutical composition, at least one kind of polyhydric alcohol selected from propylene glycol or 1,3-butylene glycol in an amount of 8% by mass to 23% by mass with respect to the entire mass of the pharmaceutical composition, benzyl alcohol in an amount of 5% by mass to 24% by mass with respect to the entire mass of the pharmaceutical composition, benzyl benzoate in an amount of 8% by mass to 19% by mass with respect to the entire mass of the pharmaceutical composition, and castor oil, and in which a content of ethanol is less than 1% by mass with respect to the entire mass of the pharmaceutical composition, and a content of benzoic acid is less than 1% by mass with respect to the entire mass of the pharmaceutical composition.

11 Claims, No Drawings

PHARMACEUTICAL COMPOSITION

CROSS-REFERENCE TO RELATED APPLICATIONS

This application is a continuation application of International Application No. PCT/JP2017/018739, filed May 18, 2017, the disclosure of which is incorporated herein by reference in its entirety. Further, this application claims priority from Japanese Patent Application No. 2016-109268, filed May 31, 2016, the disclosure of which is incorporated herein by reference in its entirety.

BACKGROUND OF THE INVENTION

1. Field of the Invention

The present invention relates to a pharmaceutical composition.

2. Description of the Related Art

Fulvestrant (7α-[9-(4,4,5,5,5-pentafluoropentylsulfinyl)nonyl]estra-1,3,5(10)-triene-3,1713-diol) is an estrogen receptor antagonist and is marketed under a trade name of FASLODEX (registered trademark) as an intramuscular injection preparation by AstraZeneca. FASLODEX is supplied in the form of a 5 mL previously-filled syringe that contains fulvestrant at an indicated amount of 50 mg/mL and contains, as additives, ethanol, benzyl alcohol, benzyl benzoate, and castor oil.

In recent years, various reports on pharmaceutical preparations containing fulvestrant have been made.

For example, JP3713237B discloses a pharmaceutical preparation suitable for intramuscular injection which contains fulvestrant, pharmaceutically acceptable alcohols (ethanol and benzyl alcohol), benzyl benzoate, and castor oil.

JP2004-534093A discloses a pharmaceutical preparation suitable for intramuscular injection which contains fulvestrant, pharmaceutically acceptable alcohol (ethanol and benzyl alcohol), propylene glycol, and castor oil.

JP2009-509942A discloses a preparation that contains fulvestrant, pharmaceutically acceptable alcohol (ethanol and benzyl alcohol), propylene glycol or polyethylene glycol, and castor oil.

WO2015/033302A discloses a preparation that contains fulvestrant, benzoic acid, alcohol (ethanol), and vegetable oil.

JP2011-514349A discloses a fulvestrant blend for intramuscular injection which contains fulvestrant, glycofurol, propylene glycol, polyethylene glycol, and the like and contains substantially no castor oil.

SUMMARY OF THE INVENTION

By the way, fulvestrant is a drug which shows a poor solubility in water. Therefore, in the related art, ethanol is used as a solvent in a pharmaceutical preparation containing fulvestrant.

However, use of ethanol in a pharmaceutical preparation causes the pharmaceutical preparation to have a limitation on administration to a patient who develops an allergic reaction to ethanol such as alcohol hypersensitivity, which is not preferable from the viewpoint of application to a wide range of patients.

Regarding the above-described points, the pharmaceutical preparations described in JP3713237B and JP2004-534093A contain a high concentration of ethanol in order that fulvestrant is blended at a high concentration. In addition, in the pharmaceutical preparations described in JP2009-509942A and WO2015/033302A, the preparations are made without using a non-aqueous ester solvent (benzyl benzoate or the like) in which fulvestrant has good dissolution properties, and attention is not paid to elimination of use of ethanol.

Accordingly, it is difficult to administer the pharmaceutical preparations described in JP3713237B, JP2004-534093A, JP2009-509942A, and WO2015/033302A to a patient who develops an allergic reaction to ethanol.

On the other hand, in the pharmaceutical preparation described in JP2011-514349A, the preparation is made without using ethanol. Thus, it is possible to administer the pharmaceutical preparation to a patient who develops an allergic reaction to ethanol. However, the pharmaceutical preparation described in JP2011-514349A contains substantially no castor oil. Thus, for example, in a case where intramuscular administration thereof is performed, it is difficult to maintain a therapeutically effective blood fulvestrant concentration for a certain period of time, and thus it cannot be said to be a therapeutically appropriate pharmaceutical preparation.

In addition, in selecting a solvent which is substituted for ethanol (hereinafter also referred to as "alternative solvent"), it is necessary to consider not only dissolution properties of fulvestrant in the alternative solvent but also compatibility of the alternative solvent with other ingredients to be contained (for example, a solvent such as castor oil). In particular, for an injectable liquid preparation, in a case where ingredients contained therein do not have a good compatibility, in storage at a low temperature, turbidity can occur due to phase separation or precipitation, which is not preferable.

One embodiment of the present invention has been made in view of the circumstances as described above, and an object of the present invention is to provide a pharmaceutical composition which contains substantially no ethanol, and in which fulvestrant has good dissolution properties and occurrence of turbidity is suppressed in a case of being stored at a low temperature.

Specific means for achieving the above-mentioned object includes the following embodiments.

[1] A pharmaceutical composition comprising:
 fulvestrant;
 at least one kind of polyhydric alcohol selected from propylene glycol or 1,3-butylene glycol;
 benzyl alcohol;
 benzyl benzoate; and
 castor oil,
 in which the pharmaceutical composition satisfies the following requirements (1) to (6).

(1) a content of ethanol is less than 1% by mass with respect to the entire mass of the pharmaceutical composition (2) a content of benzoic acid is less than 1% by mass with respect to the entire mass of the pharmaceutical composition (3) a content of the fulvestrant is 4.5% by mass to 10.0% by mass with respect to the entire mass of the pharmaceutical composition (4) a content of the at least one kind of polyhydric alcohol selected from propylene glycol or 1,3-butylene glycol is 8% by mass to 23% by mass with respect to the entire mass of the pharmaceutical composition (5) a content of benzyl alcohol is 5% by mass to 24% by mass with respect to the entire mass of the pharmaceutical composition (6) a content of benzyl benzoate is 8% by mass to 19% by mass with respect to the entire mass of the pharmaceutical composition

[2] The pharmaceutical composition according to [1], in which the content of ethanol is less than 0.5% by mass with respect to the entire mass of the pharmaceutical composition.

[3] The pharmaceutical composition according to [1] or [2], in which the at least one kind of polyhydric alcohol selected from propylene glycol or 1,3-butylene glycol is propylene glycol.

[4] The pharmaceutical composition according to [3], in which a content of propylene glycol is 12% by mass to 18% by mass with respect to the entire mass of the pharmaceutical composition.

[5] The pharmaceutical composition according to any one of [1] to [4], in which the content of benzyl alcohol is 5% by mass to 15% by mass with respect to the entire mass of the pharmaceutical composition.

[6] The pharmaceutical composition according to any one of [1] to [5], in which the content of benzyl benzoate is 10% by mass to 16% by mass with respect to the entire mass of the pharmaceutical composition.

[7] A pharmaceutical composition comprising:
fulvestrant;
propylene glycol;
benzyl alcohol;
benzyl benzoate; and
castor oil,
in which the pharmaceutical composition satisfies the following requirements (i) to (vi).

(i) a content of ethanol is less than 0.5% by mass with respect to the entire mass of the pharmaceutical composition (ii) a content of benzoic acid is less than 1% by mass with respect to the entire mass of the pharmaceutical composition (iii) a content of fulvestrant is 4.5% by mass to 10.0% by mass with respect to the entire mass of the pharmaceutical composition (iv) a content of propylene glycol is 12% by mass to 18% by mass with respect to the entire mass of the pharmaceutical composition (v) a content of benzyl alcohol is 5% by mass to 15% by mass with respect to the entire mass of the pharmaceutical composition (vi) a content of benzyl benzoate is 10% by mass to 16% by mass with respect to the entire mass of the pharmaceutical composition

[8] The pharmaceutical composition according to any one of [1] to [7], which is for intramuscular injection.

According to one embodiment of the present invention, there is provided a pharmaceutical composition which contains substantially no ethanol, and in which fulvestrant has good dissolution properties and occurrence of turbidity is suppressed in a case of being stored at a low temperature.

DESCRIPTION OF THE PREFERRED EMBODIMENTS

Hereinafter, an example of an embodiment of a pharmaceutical composition to which the present invention is applied will be described. However, the present invention is not limited to the following embodiment at all, and it is possible to practice the present invention with appropriate modifications within a scope of a purpose of one embodiment of the present invention.

In the present specification, a numerical range expressed using "to" means a range including numerical values described before and after the preposition "to" as a minimum value and a maximum value, respectively.

In numerical ranges described in a stepwise manner in the present specification, an upper limit value or a lower limit value described in one numerical range may be replaced with an upper limit value or a lower limit value of another numerical range described in a stepwise manner. In addition, in a numerical range described in the present specification, an upper limit value or a lower limit value described in the numerical range may be replaced with values shown in Examples.

In the present specification, in a case where a plurality of substances corresponding to each ingredient is present in a pharmaceutical composition, unless otherwise specified, an amount of each ingredient in the pharmaceutical composition means a total amount of the plurality of substances present in the pharmaceutical composition.

In the present specification, the term "step" includes not only an independent step, but also steps in a case where an intended purpose of the step is achieved even though it is not possible to make a clear distinction from the other step.

In the present specification, "low temperature" generally refers to a temperature applied in a case where a pharmaceutical composition containing fulvestrant as an active ingredient is refrigerated and stored, and specifically means a range of 2° C. to 8° C.

In the present specification, "to contain substantially no ethanol" means that a content of ethanol is less than 1% by mass with respect to the entire mass of the pharmaceutical composition.

Pharmaceutical Composition

The pharmaceutical composition of the present embodiment is a pharmaceutical composition which contains fulvestrant, at least one kind of polyhydric alcohol (hereinafter also referred to as "specific polyhydric alcohol") selected from propylene glycol or 1,3-butylene glycol, benzyl alcohol, benzyl benzoate, and castor oil, and satisfies the following requirements (1) to (6).

(1) A content of ethanol is less than 1% by mass with respect to the entire mass of the pharmaceutical composition.

(2) A content of benzoic acid is less than 1% by mass with respect to the entire mass of the pharmaceutical composition.

(3) A content of the fulvestrant is 4.5% by mass to 10.0% by mass with respect to the entire mass of the pharmaceutical composition.

(4) A content of the at least one kind of polyhydric alcohol selected from propylene glycol or 1,3-butylene glycol is 8% by mass to 23% by mass with respect to the entire mass of the pharmaceutical composition.

(5) A content of benzyl alcohol is 5% by mass to 24% by mass with respect to the entire mass of the pharmaceutical composition.

(6) A content of benzyl benzoate is 8% by mass to 19% by mass with respect to the entire mass of the pharmaceutical composition.

Fulvestrant, which is an active ingredient in the pharmaceutical composition of the present embodiment, is a drug which shows a poor solubility in water. Therefore, in pharmaceutical preparations containing the fulvestrant in the related art, as a solvent in which the fulvestrant has good dissolution properties, ethanol is selected.

However, use of ethanol in a pharmaceutical preparation causes the pharmaceutical preparation to have a limitation on administration to a patient who develops an allergic reaction to ethanol such as alcohol hypersensitivity, which is not preferable from the viewpoint of application to a wide range of patients.

On the other hand, in selecting an alternative solvent for ethanol, it is necessary to consider not only dissolution properties of the fulvestrant in an alternative solvent but also compatibility of the alternative solvent with other ingredients to be contained (for example, a solvent such as castor oil). In particular, for an injectable liquid preparation, in a case where ingredients contained therein do not have a good compatibility, in a case of being stored at a low temperature, turbidity can occur due to phase separation or precipitation.

The pharmaceutical composition of the present embodiment contains the fulvestrant in an amount of 4.5% by mass to 10.0% by mass with respect to the entire mass of the pharmaceutical composition, the at least one kind of polyhydric alcohol selected from propylene glycol or 1,3-butylene glycol in an amount of 8% by mass to 23% by mass with respect to the entire mass of the pharmaceutical composition, benzyl alcohol in an amount of 5% by mass to 24% by mass with respect to the entire mass of the pharmaceutical composition, benzyl benzoate in an amount of 8% by mass to 19% by mass with respect to the entire mass of the pharmaceutical composition, and castor oil, in which by setting a content of benzoic acid to be less than 1% by mass with respect to the entire mass of the pharmaceutical composition, even in a case where a content of ethanol is less than 1% by mass with respect to the entire mass of the pharmaceutical composition, that is, substantially no ethanol is contained, the fulvestrant exhibits good dissolution properties. In other words, in the pharmaceutical composition of the present embodiment, it is possible to contain the fulvestrant at a high concentration (for example, in an amount of 10.0% by mass with respect to the entire mass of the pharmaceutical composition) even in a case where substantially no ethanol is contained. In addition, in the pharmaceutical composition of the present embodiment, the abovementioned ingredients which are contained in the pharmaceutical composition have a good compatibility. Thus, it is considered that occurrence of turbidity is suppressed even in a case of being stored at a low temperature.

<Ethanol>

In the pharmaceutical composition of the present embodiment, a content of ethanol is less than 1% by mass with respect to the entire mass of the pharmaceutical composition.

Since the content of ethanol in the pharmaceutical composition of the present embodiment is less than 1% by mass with respect to the entire mass of the pharmaceutical composition, it is possible to apply the pharmaceutical composition to even a patient who develops an allergic reaction to ethanol such as alcohol hypersensitivity. Accordingly, the pharmaceutical composition of the present embodiment can be administered to a wide range of patients including a patient who develops an allergic reaction to ethanol.

In general, in a pharmaceutical composition containing ethanol which is a volatile ingredient, there may be a case where a composition of the pharmaceutical composition changes due to volatilization of ethanol during a production step of the pharmaceutical composition, a distribution step thereof as a product, or the like. A compositional change in the pharmaceutical composition due to volatilization of ethanol causes, for example, expression of unexpected fluctuations of a clinical effect or side effects after administration, which is not preferable. In addition, as a concentration of fulvestrant in the pharmaceutical composition is increased due to volatilization of ethanol, a deviation from a quality standard may occur.

In the pharmaceutical composition of the present embodiment, a content of ethanol is less than 1% by mass with respect to the entire mass of the pharmaceutical composition. Thus, a compositional change in the pharmaceutical composition which can occur due to volatilization of ethanol during a production step or storage, in particular, a concentration change of the fulvestrant is decreased or suppressed.

Furthermore, in the pharmaceutical composition of the present embodiment, since the content of ethanol is less than 1% by mass with respect to the entire mass of the pharmaceutical composition, a burden on an operator and an environment due to volatilization of ethanol is decreased or suppressed, and an excellent production suitability is exhibited.

The content of ethanol in the pharmaceutical composition of the present embodiment is preferably less than 0.5% by mass, more preferably less than 0.3% by mass, and even more preferably less than 0.1% by mass, with respect to the entire mass of the pharmaceutical composition, and particularly preferably the pharmaceutical composition does not contain ethanol, that is, the content of ethanol is 0% by mass.

Hereinafter, the respective ingredients of the pharmaceutical composition of the present embodiment will be described in detail.

<Fulvestrant>

The pharmaceutical composition of the present embodiment contains fulvestrant as an active ingredient.

Fulvestrant (7α[9-(4,4,5,5,5-pentafluoropentylsulfinyl)nonyl]estra-1,3, 5(10)-triene-3,17β-diol) is an estrogen receptor antagonist and is known as a drug for treating breast cancer.

A content of the fulvestrant in the pharmaceutical composition of the present embodiment is 4.5% by mass to 10.0% by mass.

From the viewpoint of a single dose, the content of the fulvestrant in the pharmaceutical composition of the present embodiment is preferably 4.5% by mass to 7.0% by mass, more preferably 4.5% by mass to 5.5% by mass, and even more preferably 5% by mass to 5.5% by mass, with respect to the entire mass of the pharmaceutical composition.

<Specific Polyhydric Alcohol>

The pharmaceutical composition of the present embodiment contains at least one kind of polyhydric alcohol (that is, specific polyhydric alcohol) selected from propylene glycol or 1,3-butylene glycol.

In the pharmaceutical composition of the present embodiment, the specific polyhydric alcohol contributes to dissolution properties of fulvestrant.

The pharmaceutical composition of the present embodiment may contain, as the specific polyhydric alcohol, only propylene glycol, only 1,3-butylene glycol, or both of propylene glycol and 1,3-butylene glycol.

From the viewpoint of further increasing dissolution properties of fulvestrant, the pharmaceutical composition of the present embodiment preferably contains at least propylene glycol as the specific polyhydric alcohol, and it is particularly preferable that the specific polyhydric alcohol is propylene glycol.

A content of the specific polyhydric alcohol in the pharmaceutical composition of the present embodiment is 8% by mass to 23% by mass with respect to the entire mass of the pharmaceutical composition.

In a case where the content of the specific polyhydric alcohol in the pharmaceutical composition of the present embodiment is equal to or greater than 8% by mass with respect to the entire mass of the pharmaceutical composition, dissolution properties of fulvestrant become good, and there is a tendency that occurrence of turbidity due to precipitation of fulvestrant in a pharmaceutical composition is suppressed in a case of being stored at a low temperature. From the viewpoint of suppressing occurrence of such turbidity, the content of the specific polyhydric alcohol in the pharmaceutical composition of the present embodiment is preferably equal to or greater than 10% by mass, more preferably equal to or greater than 12% by mass, and more preferably equal to or greater than 14% by mass, with respect to the entire mass of the pharmaceutical composition.

In a case where the content of the specific polyhydric alcohol in the pharmaceutical composition of the present embodiment is equal to or less than 23% by mass with respect to the entire mass of the pharmaceutical composition, for example, the specific polyhydric alcohol and castor oil are sufficiently compatible with each other. Thus, in a case of being stored at a low temperature, there is a tendency that occurrence of turbidity due to phase separation is suppressed in the pharmaceutical composition. From the viewpoint of suppressing occurrence of such turbidity, the content of the specific polyhydric alcohol in the pharmaceutical composition of the present embodiment is preferably equal to or less than 20% by mass and more preferably equal to or less than 18% by mass, with respect to the entire mass of the pharmaceutical composition.

<Benzyl Alcohol>

The pharmaceutical composition of the present embodiment contains benzyl alcohol.

In the pharmaceutical composition of the present embodiment, benzyl alcohol contributes to dissolution properties of fulvestrant.

A content of benzyl alcohol in the pharmaceutical composition of the present embodiment is 5% by mass to 24% by mass with respect to the entire mass of the pharmaceutical composition.

In a case where the content of benzyl alcohol in the pharmaceutical composition of the present embodiment is equal to or greater than 5% by mass with respect to the entire mass of the pharmaceutical composition, dissolution properties of fulvestrant becomes good, and there is a tendency that occurrence of turbidity due to precipitation of fulvestrant in a pharmaceutical composition is suppressed in a case of being stored at a low temperature. From the viewpoint of suppressing occurrence of such turbidity, the content of benzyl alcohol in the pharmaceutical composition of the present embodiment is preferably equal to or greater than 6% by mass and more preferably equal to or greater than 8% by mass, with respect to the entire mass of the pharmaceutical composition.

In a case where the content of benzyl alcohol in the pharmaceutical composition of the present embodiment is equal to or less than 24% by mass with respect to the entire mass of the pharmaceutical composition, for example, benzyl alcohol and castor oil are sufficiently compatible with each other. Thus, in a case of being stored at a low temperature, there is a tendency that occurrence of turbidity due to phase separation is suppressed in the pharmaceutical composition. From the viewpoint of suppressing occurrence of such turbidity, the content of benzyl alcohol in the pharmaceutical composition of the present embodiment is preferably equal to or less than 20% by mass, more preferably equal to or less than 18% by mass, and even more preferably equal to or less than 15% by mass, with respect to the entire mass of the pharmaceutical composition.

<Benzyl Benzoate>

The pharmaceutical composition of the present embodiment contains benzyl benzoate.

In the pharmaceutical composition of the present embodiment, benzyl benzoate contributes to dissolution properties of fulvestrant and suppressed occurrence of turbidity in the pharmaceutical composition in a case of being stored at a low temperature.

A content of benzyl benzoate in the pharmaceutical composition of the present embodiment is 8% by mass to 19% by mass with respect to the entire mass of the pharmaceutical composition.

In a case where the content of benzyl benzoate in the pharmaceutical composition of the present embodiment is equal to or greater than 8% by mass with respect to the entire mass of the pharmaceutical composition, dissolution properties of fulvestrant becomes good, and there is a tendency that occurrence of turbidity due to precipitation of fulvestrant in a pharmaceutical composition is suppressed in a case of being stored at a low temperature. From the viewpoint of suppressing occurrence of such turbidity, the content of benzyl benzoate in the pharmaceutical composition of the present embodiment is preferably equal to or greater than 9% by mass and more preferably equal to or greater than 10% by mass, with respect to the entire mass of the pharmaceutical composition.

In a case where the content of benzyl benzoate in the pharmaceutical composition of the present embodiment is equal to or less than 19% by mass with respect to the entire mass of the pharmaceutical composition, for example, benzyl alcohol and castor oil are sufficiently compatible with each other. Thus, in a case of being stored at a low temperature, there is a tendency that occurrence of turbidity due to phase separation is suppressed in the pharmaceutical composition. From the viewpoint of suppressing occurrence of such turbidity, the content of benzyl benzoate in the pharmaceutical composition of the present embodiment is preferably equal to or less than 16% by mass and more preferably equal to or less than 15% by mass, with respect to the entire mass of the pharmaceutical composition.

<Castor Oil>

The pharmaceutical composition of the present embodiment contains castor oil.

Due to containing castor oil, the pharmaceutical composition of the present embodiment allows a therapeutically effective blood fulvestrant concentration to be maintained for a certain period of time.

A content of castor oil in the pharmaceutical composition of the present embodiment is not particularly limited.

From the viewpoint of maintaining dissolution properties of fulvestrant, the content of castor oil in the pharmaceutical composition of the present embodiment is, for example, preferably equal to or greater than 40% by mass, more preferably equal to or greater than 45% by mass, even more preferably equal to or greater than 50% by mass, and particularly preferably equal to or greater than 55% by mass, with respect to the entire mass of the pharmaceutical composition. In addition, from the viewpoint of increasing a storage stability of the pharmaceutical composition, the content of castor oil in the pharmaceutical composition of the present embodiment is preferably equal to or less than 70% by mass, more preferably equal to or less than 65% by mass, and particularly preferably equal to or less than 60% by mass.

In a case where the content of castor oil in the pharmaceutical composition of the present embodiment is 40% by mass to 70% by mass with respect to the entire mass of the pharmaceutical composition, for example, a therapeutically effective blood fulvestrant concentration can be maintained for a certain period of time, and blending amounts of ingredients to be contained other than castor oil which are necessary to uniformly dissolve fulvestrant can be secured.

<Benzoic Acid>

In the pharmaceutical composition of the present embodiment, a content of benzoic acid is less than 1% by mass with respect to the entire mass of the pharmaceutical composition.

The content of benzoic acid in the pharmaceutical composition of the present embodiment is preferably less than 0.5% by mass, more preferably less than 0.3% by mass, and even more preferably less than 0.1% by mass, with respect to the entire mass of the pharmaceutical composition, and particularly preferably the pharmaceutical composition does not contain benzoic acid, that is, the content of benzoic acid is 0% by mass.

(Other Additives)

The pharmaceutical composition of the present embodiment may, if necessary, further contain a pharmaceutically acceptable additive (hereinafter also referred to as "other additive"). In a case where the pharmaceutical composition of the present embodiment is applied for intramuscular injection, it is preferable to further contain an additive suitable for intramuscular injection.

As the other additive, glycerin, polyethylene glycol, ascorbic acid or a salt thereof, hydrochloric acid, gluconic acid or a salt thereof, acetic acid or a salt thereof, lactic acid or a salt thereof, boric acid or a salt thereof, phosphoric acid or a salt thereof, sulfuric acid or a salt thereof, tartaric acid or a salt thereof, citric acid or a salt thereof, potassium hydroxide, calcium hydroxide, sodium hydroxide, magnesium hydroxide, monoethanolamine, diethanolamine, triethanolamine, trometamol, meglumine, glycine, histidine or a salt thereof, ε-aminocaproic acid, arginine or a salt thereof, cysteine or a salt thereof, methionine, alanine, leucine, aspartic acid or a salt thereof, glutamic acid or a salt thereof, thioglycerin, thioglycolic acid or a salt thereof, taurine, sodium edetate, lidocaine or a salt thereof, nicotinic acid amide, chlorobutanol, creatinine, sesame oil, peanut oil, camellia oil, butylhydroxytoluene, butylhydroxyanisole, sorbitan sesquioleic acid ester, ethyl oleate, ethyl lactate, thimerosal, polysorbate 20, polysorbate 80, tocopherol, and the like are mentioned.

However, the other additive is not limited thereto.

In a case where the pharmaceutical composition of the present embodiment contains the other additives, the pharmaceutical composition may contain only one type of the other additives or may contain two or more types thereof.

In a case where the pharmaceutical composition of the present embodiment contains the other additive, a content of the other additive in the pharmaceutical composition is preferably equal to or less than 10% by mass with respect to the entire mass of the pharmaceutical composition.

(Water)

The pharmaceutical composition of the present embodiment may contain water.

In a case where the pharmaceutical composition of the present embodiment contains water, a content of water in the pharmaceutical composition is not particularly limited. For example, from the viewpoint of suppressing occurrence of turbidity in a case of being stored at a low temperature, water is preferably contained in an amount of equal to or less than 1% by mass with respect to the entire mass of the pharmaceutical composition.

Preferable Compositional Example

As preferable compositional examples of the pharmaceutical composition of the present embodiment, for example, the following compositions are mentioned. The pharmaceutical composition of the present embodiment having a composition as shown below has better dissolution properties of fulvestrant and exhibits further suppressed occurrence of turbidity in a case of being stored at a low temperature.

A composition that contains fulvestrant, propylene glycol, benzyl alcohol, benzyl benzoate, and castor oil and satisfies the following requirements (i) to (vi).

(i) A content of ethanol is less than 0.5% by mass with respect to the entire mass of the pharmaceutical composition.

(ii) A content of benzoic acid is less than 1% by mass with respect to the entire mass of the pharmaceutical composition.

(iii) A content of the fulvestrant is 4.5% by mass to 10.0% by mass with respect to the entire mass of the pharmaceutical composition.

(iv) A content of propylene glycol is 12% by mass to 18% by mass with respect to the entire mass of the pharmaceutical composition.

(v) A content of benzyl alcohol is 5% by mass to 15% by mass with respect to the entire mass of the pharmaceutical composition.

(vi) A content of benzyl benzoate is 10% by mass to 16% by mass with respect to the entire mass of the pharmaceutical composition.

[Use of Pharmaceutical Composition]

The pharmaceutical composition of the present embodiment can be suitably used for intramuscular injection.

The pharmaceutical composition of the present embodiment is a pharmaceutical preparation suitable for intramuscular injection because the fulvestrant has good dissolution properties and occurrence of turbidity due to phase separation or precipitation of ingredients contained in the pharmaceutical composition is suppressed even in a case of being stored at a low temperature (2° C. to 8° C.), so that a state in which ingredients such as the fulvestrant are well mixed is stably maintained.

In addition, due to containing the fulvestrant as an active ingredient, the pharmaceutical composition of the present embodiment can be suitably used for the treatment of breast cancer.

[Method for Producing Pharmaceutical Composition]

A method for producing the pharmaceutical composition of the present embodiment is not particularly limited as long as the method is capable of producing the aforementioned pharmaceutical composition.

As the method for producing the pharmaceutical composition of the present embodiment, from the viewpoint that it is easy to obtain a pharmaceutical composition in which ingredients contained therein are uniformly mixed, a method for producing the pharmaceutical composition of the present embodiment, which will be described below, is preferable.

A method for producing the pharmaceutical composition of the present embodiment (hereinafter also referred to as "production method of the present embodiment") has a step (hereinafter also referred to as "first step") of mixing fulvestrant, at least one kind of polyhydric alcohol (that is, specific polyhydric alcohol) selected from propylene glycol or 1,3-butylene glycol, benzyl alcohol, and benzyl benzoate, to obtain a fulvestrant-containing liquid, and a step (hereinafter also referred to as "second step") of mixing the obtained fulvestrant-containing liquid with castor oil, to obtain a pharmaceutical composition.

The production method of the present embodiment has an advantage that it is easy to obtain a pharmaceutical composition in which ingredients contained therein are uniformly mixed, as compared with a case where fulvestrant, the specific polyhydric alcohol, benzyl alcohol, benzyl benzoate, and castor oil are mixed all together.

Hereinafter, the production method of the present embodiment will be described. However, descriptions regarding matters which are common to the above-described pharmaceutical composition, for example, ingredients contained in the pharmaceutical composition and amounts thereof will be omitted.

<First Step>

The first step is a step of mixing fulvestrant, a specific polyhydric alcohol, benzyl alcohol, and benzyl benzoate to obtain a fulvestrant-containing liquid.

In a case where the pharmaceutical composition contains other ingredients as described above, it is preferable that fulvestrant, a specific polyhydric alcohol, benzyl alcohol, benzyl benzoate, and the other ingredients are mixed to obtain a fulvestrant-containing liquid.

In the first step, it is sufficient that the respective ingredients to be mixed are simply mixed, in which all the ingredients may be mixed at one time, or the respective ingredients may be divided into several portions and mixed.

A method of mixing is not particularly limited, and, for example, mixing by stirring is mentioned.

A temperature condition at the time of mixing is not particularly limited, and can be appropriately set, for example, according to a composition (types and amounts) of the ingredients to be mixed and the like.

In the first step, usually, fulvestrant, a specific polyhydric alcohol, benzyl alcohol, and benzyl benzoate are mixed under a condition of an atmospheric temperature of 15° C. to 60° C., to obtain a fulvestrant-containing liquid.

<Second Step>

The second step is a step of mixing the fulvestrant-containing liquid obtained in the first step and castor oil, to obtain a pharmaceutical composition.

A method of mixing is not particularly limited, and, for example, mixing by stirring is mentioned.

In the second step, the fulvestrant-containing liquid and castor oil may be mixed at one time, or, for example, the fulvestrant-containing liquid and castor oil may be mixed by gradually adding castor oil to the fulvestrant-containing liquid while stirring the fulvestrant-containing liquid.

A temperature condition at the time of mixing is not particularly limited.

In the second step, usually, the fulvestrant-containing liquid and castor oil are mixed under a condition of an atmospheric temperature of 15° C. to 60° C., to obtain a pharmaceutical composition.

<Other Step>

The production method of the present embodiment may, if necessary, have another step than the first step and the second step. In addition, the first step and the second step may be configured to include a plurality of steps.

As the other step, a step of sterilizing the pharmaceutical composition, a step of filling a container with the pharmaceutical composition, and the like are mentioned.

As the sterilizing step, a filter sterilization method using a sterilizing filter is preferable.

[Container for Pharmaceutical Composition]

As a container which is to be filled with the pharmaceutical composition of the present embodiment, a vial, an ampoule, a syringe, and the like are mentioned.

Among these, as the container which is to be filled with the pharmaceutical composition of the present embodiment, from the viewpoint of handleability in a medical field, a syringe is preferable, and a glass syringe is more preferable. That is, as a dosage form of the pharmaceutical composition of the present embodiment, a prefilled syringe obtained by previously filling a syringe with a pharmaceutical composition is preferable.

[Others]

Another embodiment of the present invention also encompasses a method for the treatment of breast cancer, which includes administering, to a patient to be treated for breast cancer, the above-described pharmaceutical composition containing fulvestrant as an active ingredient.

EXAMPLES

Hereinafter, the present invention will be described in more detail by way of Examples. However, the present invention is not limited to the following Examples to the extent that the present invention does not deviate from a spirit thereof.

[Production of Pharmaceutical Composition]

Example 1

5 parts by mass of fulvestrant, 14 parts by mass of propylene glycol as a specific polyhydric alcohol, 10 parts by mass of benzyl alcohol, and 15 parts by mass of benzyl benzoate were weighed into a clean glass container containing a stirring bar. Then, the mixture was stirred to obtain a fulvestrant-containing liquid. Subsequently, castor oil was added to the obtained fulvestrant-containing liquid so that a total amount was adjusted to 100 parts by mass. Then, the mixture was further stirred to become uniform, and a pharmaceutical composition of Example 1 was obtained.

Examples 2 to 16

By carrying out the same operation as in Example 1, except that the composition of the pharmaceutical composition was changed to each of compositions shown in Table 1, pharmaceutical compositions of Examples 2 to 16 were obtained.

Comparative Examples 1 to 12

By carrying out the same operation as in Example 1, except that the composition of the pharmaceutical composition was changed to each of compositions shown in Table 1, pharmaceutical compositions of Comparative Examples 1 to 12 were obtained.

Comparative Examples 13 to 29

By carrying out the same operation as in Example 1, except that the composition of the pharmaceutical composition was changed to each of compositions shown in Table 2, pharmaceutical compositions of Comparative Examples 13 to 29 were obtained.

[Evaluation]

1. Dissolution Properties of Fulvestrant

To each of the pharmaceutical compositions of Examples 1 to 16, and Comparative Examples 1 to 12 as obtained above, at least a saturated amount of fulvestrant was further added, and the mixture was stirred at a room temperature (15° C. to 30° C.) for at least one day. Then, the mixture was centrifuged at 10,000 round per minute (rpm; the same applies to the following) to 14,000 rpm for 10 to 20 minutes to remove an excess of fulvestrant (that is, fulvestrant to be precipitated), and a supernatant was obtained.

An amount of fulvestrant dissolved in the obtained supernatant was measured by high performance liquid chromatography (HPLC) under the following conditions to calculate a solubility (% by mass) of fulvestrant in the pharmaceutical composition. Then, the dissolution properties of fulvestrant were evaluated according to the following evaluation standard. The results are shown in Table 1.

In a case where an evaluation result was classified into "A", "B", or "C", the pharmaceutical composition was determined as acceptable.

Evaluation Standard

A: Solubility of fulvestrant which is equal to or greater than 5.5% by mass.

B: Solubility of fulvestrant which is equal to or greater than 5.0% by mass and less than 5.5% by mass.

C: Solubility of fulvestrant which is equal to or greater than 4.5% by mass and less than 5.0% by mass.

D: Solubility of fulvestrant which is equal to or greater than 4.0% by mass and less than 4.5% by mass.

E: Solubility of fulvestrant which is less than 4.0% by mass.

In the above evaluation test, a higher solubility value of fulvestrant indicates a pharmaceutical composition which is capable of having a higher ability to sufficiently and uniformly contain fulvestrant necessary for treatment and of containing fulvestrant at a higher concentration.

The fact that the solubility of fulvestrant is less than 5.0% by mass means that the fulvestrant in a pharmaceutical composition before further addition of fulvestrant was in a state of being dissolved beyond an original solubility thereof (a so-called supersaturated state). That is, an excess of fulvestrant which exceeds the solubility thereof in the pharmaceutical composition was precipitated by further addition of fulvestrant.

—HPLC Conditions—

Column: XBridge C8 (product name, particle diameter: 3.5 μm, column size: 4.6 mm×150 mm, Waters Corporation)

Mobile phase A: methanol/water=70/30

Mobile phase B: Methanol

Gradient condition (proportion of mobile phase B): 0% (start)→0% (12 min)→100% (12.1 min)→100% (20 min) →0% (20.1 min)=0% (30 min, stop)

Detection wavelength: 225 nm

Flow rate: 1.0 mL/min

Column temperature: 40° C.

2. Presence or Absence of Turbidity

Regarding each of the pharmaceutical compositions of Examples 1 to 16, Comparative Examples 1 to 4, and Comparative Example 7 as obtained above, at least 1 mL thereof was weighed and taken into each colorless transparent glass bottle (5 mL volume), and stored in a refrigerator (atmospheric temperature: 2° C. to 8° C.). After 1 hour or longer had passed from the start of storage, the glass bottle was taken out from the refrigerator. Immediately after being taken out, cloudiness formed on a surface of the glass bottle was wiped off with Kimwipe (registered trademark), and then the pharmaceutical composition placed in the glass bottle was visually observed to identify presence or absence of turbidity. The results are shown in Table 1.

In Table 1, a case where turbidity is not identified in the pharmaceutical composition placed in the glass bottle was denoted as "absent", and a case where turbidity is identified was denoted as "present".

For each of the pharmaceutical compositions of Comparative Example 5, Comparative Example 6, and Comparative Examples 8 to 12, since an evaluation result in the "1. Dissolution properties of fulvestrant" was "D" or "E", an evaluation test on presence or absence of turbidity was not carried out.

In the above evaluation, a state in which turbidity is not identified in the pharmaceutical composition placed in the glass bottle (that is, the pharmaceutical composition is clear) indicates a state in which the ingredients contained therein are uniformly mixed, meaning that no phase separation or precipitation occurs in the ingredients contained in the pharmaceutical composition during storage at a low temperature (2° C. to 8° C.), and a state in which the ingredients such as fulvestrant are well mixed is stably retained.

On the other hand, a state in which turbidity is identified in the pharmaceutical composition contained in the glass bottle indicates a state in which the ingredients contained therein are not uniformly mixed, meaning that any of the ingredients contained in the pharmaceutical composition is phase-separated or precipitated during storage at a low temperature (2° C. to 8° C.), and the pharmaceutical composition is not a preparation suitable for intramuscular injection.

3. Compositional Stability (1) Measurement in open state

A mass (g) of each of 5 mL-volume glass vial bottles (model: SV-5, Nichiden Rika Glass Co., Ltd.) was measured, and the measured value was recorded. Subsequently, about 0.1 g of each of the pharmaceutical compositions of Example 1, Example 3, Examples 14 to 16, and Comparative Examples 13 to 29 as obtained above was weighed and taken into the above vial bottle. Then, a mass (g) of the vial bottle in which the pharmaceutical composition was placed was measured, and the measured value was recorded.

Subsequently, the vial bottle in which the pharmaceutical composition was placed was covered, at an opening part of the vial bottle, using a bolting cloth (model number: N-No. 230T, 230 mesh, NBC Mesh Tech Co., Ltd.), and left to stand in a draft chamber having an atmospheric temperature of 25° C. 6 hours after being left to stand, the vial bottle was taken out from the draft chamber, and the bolting cloth was removed. A mass (g) of the vial bottle in which the pharmaceutical composition was placed was measured again, and the measured value was recorded.

From the mass (g) of the vial bottle, and the masses (g) of the vial bottle in which the pharmaceutical composition was placed before and after lapse of time, a mass reduction rate (%) of the pharmaceutical composition is calculated based on Equation (1). Then, from a value of the calculated mass reduction rate (%) of the pharmaceutical composition, a compositional stability of the pharmaceutical composition was evaluated based on the following evaluation standard. The results are shown in Table 2.

Mass reduction rate (%) of pharmaceutical composition=[[mass (g) of vial bottle in which pharmaceutical composition is placed before lapse of time]−[mass (g) of vial bottle in which pharmaceutical composition is placed after lapse of time]/[mass (g) of vial bottle in which pharmaceutical composition is placed before lapse of time]−[mass (g) of vial bottle]]×100     Equation (1)

Evaluation Standard

A: Mass reduction rate in pharmaceutical composition which is less than 0.5%.

B: Mass reduction rate in pharmaceutical composition which is equal to or greater than 0.5% and less than 1.0%.

C: Mass reduction rate in pharmaceutical composition which is equal to or greater than 1.0% and less than 10.0%.

D: Mass reduction rate in pharmaceutical composition which is equal to or greater than 10.0%.

(2) Measurement in Syringe-filled State

A mass (g) of each of 1 mL-volume polypropylene syringes (model: SS-01T, Terumo Corporation) was measured, and the measured value was recorded. Subsequently, the syringe was filled with about 1 g of each of the pharmaceutical compositions of Example 1, Example 3, Examples 14 to 16, and Comparative Examples 13 to 29 as obtained above. Then, a mass (g) of the syringe filled with the pharmaceutical composition was measured, and the measured value was recorded.

Subsequently, the syringe filled with the pharmaceutical composition was stored in a constant-temperature tank at 50° C. 60 hours after storage, the syringe was taken out from the constant-temperature tank. A mass (g) of the syringe filled with the pharmaceutical composition was measured again, and the measured value was recorded.

From the mass (g) of the syringe, and the masses (g) of the syringe filled with the pharmaceutical composition before and after lapse of time, a mass reduction rate (%) of the pharmaceutical composition is calculated based on Equation (2). Then, from a value of the calculated mass reduction rate (%) of the pharmaceutical composition, a compositional stability of the pharmaceutical composition was evaluated based on the following evaluation standard. The results are shown in Table 2.

Mass reduction rate (%) of pharmaceutical composition=[[mass (g) of syringe filled with pharmaceutical composition before lapse of time]−[mass (g) of syringe filled with pharmaceutical composition after lapse of time]/[mass (g) of syringe filled with pharmaceutical composition before lapse of time]−[mass (g) of syringe]]×100     Equation (2)

Evaluation Standard

A: Mass reduction rate in pharmaceutical composition which is less than 0.5%.

B: Mass reduction rate in pharmaceutical composition which is equal to or greater than 0.5% and less than 1.0%.

C: Mass reduction rate in pharmaceutical composition which is equal to or greater than 1.0% and less than 10.0%.

D: Mass reduction rate in pharmaceutical composition which is equal to or greater than 10.0%.

(3) Overall Evaluation

In both the above (1) and (2), in a case where the evaluation result is [A] or [B], it was determined that a compositional stability of the pharmaceutical composition is "good". In at least one of the above (1) or (2), in a case where the evaluation result is [C] or [D], it was determined that a compositional stability of the pharmaceutical composition is "poor".

TABLE 1

| | | Composition (% by mass) | | | | | | Evaluation test | |
| | | | | | | | | Dissolution properties | Presence or absence of turbidity |
| | FLV | EtOH | BA | PG | BnOH | BnBz | Castor oil | | |
|---|---|---|---|---|---|---|---|---|---|
| Example 1 | 5 | 0 | 0 | 14 | 10 | 15 | Up to 100 | A | Absent |
| Example 2 | 5 | 0 | 0 | 16 | 8 | 15 | Up to 100 | A | Absent |
| Example 3 | 5 | 0 | 0 | 18 | 6 | 15 | Up to 100 | A | Absent |
| Example 4 | 5 | 0 | 0 | 12 | 12 | 15 | Up to 100 | A | Absent |
| Example 5 | 5 | 0 | 0 | 10 | 14 | 15 | Up to 100 | A | Absent |
| Example 6 | 5 | 0 | 0 | 15 | 12 | 12 | Up to 100 | A | Absent |
| Example 7 | 5 | 0 | 0 | 12 | 15 | 12 | Up to 100 | A | Absent |
| Example 8 | 5 | 0 | 0 | 18 | 9 | 12 | Up to 100 | A | Absent |
| Example 9 | 5 | 0 | 0 | 12 | 9 | 18 | Up to 100 | B | Absent |
| Example 10 | 5 | 0 | 0 | 9 | 12 | 18 | Up to 100 | B | Absent |
| Example 11 | 5 | 0 | 0 | 15 | 6 | 18 | Up to 100 | B | Absent |
| Example 12 | 5 | 0 | 0 | 18 | 12 | 9 | Up to 100 | A | Absent |
| Example 13 | 5 | 0 | 0 | 16 | 15 | 8 | Up to 100 | A | Absent |
| Example 14 | 5 | 0 | 0 | 8 | 23 | 8 | Up to 100 | A | Absent |
| Example 15 | 5 | 0 | 0 | 16 | 15 | 15 | Up to 100 | A | Absent |
| Example 16 | 5 | 0 | 0 | 14 | 10 | 12 | Up to 100 | A | Absent |
| Comparative Example 1 | 5 | 0 | 0 | 39 | 0 | 0 | Up to 100 | A | Present |
| Comparative Example 2 | 5 | 0 | 0 | 32 | 7 | 0 | Up to 100 | A | Present |
| Comparative Example 3 | 5 | 0 | 0 | 24 | 7 | 8 | Up to 100 | A | Present |
| Comparative Example 4 | 5 | 0 | 0 | 9 | 9 | 21 | Up to 100 | C | Present* |
| Comparative Example 5 | 5 | 0 | 0 | 32 | 0 | 7 | Up to 100 | D | NT |
| Comparative Example 6 | 5 | 0 | 0 | 24 | 0 | 15 | Up to 100 | D | NT |
| Comparative Example 7 | 5 | 0 | 0 | 16 | 0 | 23 | Up to 100 | C | Present* |
| Comparative | 5 | 0 | 0 | 8 | 0 | 31 | Up to 100 | E | NT |

TABLE 1-continued

|  | Composition (% by mass) | | | | | | Evaluation test | |
|---|---|---|---|---|---|---|---|---|
|  | | | | | | | Dissolution | Presence or absence of |
|  | FLV | EtOH | BA | PG | BnOH | BnBz | Castor oil | properties | turbidity |
| Example 8 Comparative Example 9 | 5 | 0 | 0 | 8 | 7 | 24 | Up to 100 | D | NT |
| Comparative Example 10 | 5 | 0 | 0 | 0 | 8 | 31 | Up to 100 | E | NT |
| Comparative Example 11 | 5 | 0 | 0 | 0 | 16 | 23 | Up to 100 | E | NT |
| Comparative Example 12 | 5 | 0 | 0 | 0 | 24 | 15 | Up to 100 | D | NT |

*Precipitation of fine crystal

TABLE 2

|  | Composition (% by mass) | | | | | | | Evaluation test Compositional stability | | |
|---|---|---|---|---|---|---|---|---|---|---|
|  | | | | | | | | Open state | Syringe-filled state | Overall |
|  | FLV | EtOH | BA | PG | BnOH | BnBz | Castor oil | (25° C., 6 hr) | (50° C., 60 hr) | evaluation |
| Example 1 | 5 | 0 | 0 | 14 | 10 | 15 | Up to 100 | A | A | Good |
| Example 3 | 5 | 0 | 0 | 18 | 6 | 15 | Up to 100 | A | A | Good |
| Example 14 | 5 | 0 | 0 | 8 | 23 | 8 | Up to 100 | A | A | Good |
| Example 15 | 5 | 0 | 0 | 16 | 15 | 15 | Up to 100 | A | A | Good |
| Example 16 | 5 | 0 | 0 | 14 | 10 | 12 | Up to 100 | A | A | Good |
| Comparative Example 13 | 5 | 2 | 0 | 14 | 10 | 13 | Up to 100 | C | C | Poor |
| Comparative Example 14 | 5 | 5 | 0 | 14 | 10 | 10 | Up to 100 | C | C | Poor |
| Comparative Example 15 | 5 | 6 | 0 | 14 | 10 | 9 | Up to 100 | C | C | Poor |
| Comparative Example 16 | 5 | 10 | 0 | 14 | 10 | 5 | Up to 100 | C | C | Poor |
| Comparative Example 17 | 5 | 8 | 0 | 15 | 12 | 0 | Up to 100 | C | C | Poor |
| Comparative Example 18 | 5 | 9 | 0 | 15 | 11 | 0 | Up to 100 | C | C | Poor |
| Comparative Example 19 | 5 | 10 | 0 | 15 | 10 | 0 | Up to 100 | C | C | Poor |
| Comparative Example 20 | 5 | 11 | 0 | 15 | 9 | 0 | Up to 100 | C | C | Poor |
| Comparative Example 21 | 5 | 12 | 0 | 15 | 8 | 0 | Up to 100 | D | C | Poor |
| Comparative Example 22 | 5 | 15 | 0 | 15 | 5 | 0 | Up to 100 | D | C | Poor |
| Comparative Example 23 | 5 | 10 | 0 | 13 | 12 | 0 | Up to 100 | C | C | Poor |
| Comparative Example 24 | 5 | 11 | 0 | 13 | 11 | 0 | Up to 100 | D | C | Poor |
| Comparative Example 25 | 5 | 12 | 0 | 13 | 10 | 0 | Up to 100 | D | C | Poor |
| Comparative Example 26 | 5 | 15 | 0 | 10 | 10 | 0 | Up to 100 | D | C | Poor |
| Comparative Example 27 | 5 | 12.5 | 0 | 10 | 12.5 | 0 | Up to 100 | D | C | Poor |
| Comparative Example 28 | 5 | 10 | 0 | 10 | 15 | 0 | Up to 100 | C | C | Poor |
| Comparative Example 29 | 5 | 10 | 0 | 0 | 10 | 15 | Up to 100 | C | C | Poor |

In Tables 1 and 2, "fulvestrant" was denoted as "FLV", "propylene glycol" as "PG", "benzyl alcohol" as "BnOH", "benzyl benzoate" as "BnBz", "ethanol" as "EtOH", and "benzoic acid" as "BA".

In Table 1, "NT" means that no test was conducted.

As shown in Table 1, in the pharmaceutical compositions of Examples 1 to 16, the fulvestrant had good dissolution properties and occurrence of turbidity due to phase separation or precipitation of ingredients contained in the pharmaceutical composition is suppressed even in a case of being stored at a low temperature, so that a state in which ingredients such as the fulvestrant are well mixed was stably maintained. In particular, in the pharmaceutical compositions of Examples 1 to 8 and Examples 12 to 16, the fulvestrant had the solubility of equal to or greater than 5.5% by mass, and the fulvestrant could be contained at a high concentration.

On the other hand, in the pharmaceutical compositions of Comparative Examples 1 to 12, a good result was not obtained in at least one evaluation of the dissolution properties of fulvestrant or the presence or absence of turbidity.

As shown in Table 2, for the pharmaceutical compositions of Example 1, Example 3, and Examples 14 to 16 in which a content of ethanol was less than 1% by mass, even in a case of being placed in a container in an open state and left to stand at 25° C. for 6 hours, no mass reduction was recognized. In addition, for the pharmaceutical compositions of Example 1, Example 3, and Examples 14 to 16, in a case of being stored at 50° C. for 60 hours in a syringe-filled state, almost no mass reduction was recognized.

From these results, it was found that the pharmaceutical compositions of Example 1, Example 3, and Examples 14 to 16 exhibit a small compositional change due to volatilization of an ingredient and an excellent compositional stability.

On the other hand, the pharmaceutical compositions of Comparative Examples 13 to 29 in which a content of ethanol was equal to or greater than 1% by mass exhibit a high mass reduction rate and an inferior compositional stability, as compared with the pharmaceutical compositions of Example 1, Example 3, and Examples 14 to 16 in which a content of ethanol was less than 1% by mass.

Disclosure of Japan Patent Application No. 2016-109268 filed May 31, 2016 is hereby incorporated by reference in its entirety.

All publications, patent applications, and technical standards described in the present specification are herein incorporated by reference to the same extent as a case where each individual publication, patent application, or technical standard was specifically and individually indicated to be incorporated by reference.

What is claimed is:

1. A pharmaceutical composition comprising:
fulvestrant;
propylene glycol;
benzyl alcohol;
benzyl benzoate; and
castor oil,
wherein the pharmaceutical composition satisfies the following requirements (1) to (6);
(1) a content of ethanol is less than 1% by mass with respect to the entire mass of the pharmaceutical composition;
(2) a content of benzoic acid is less than 1% by mass with respect to the entire mass of the pharmaceutical composition;
(3) a content of the fulvestrant is 4.5% by mass to 10.0% by mass with respect to the entire mass of the pharmaceutical composition;
(4) a content of the propylene glycol is 8% by mass to 23% by mass with respect to the entire mass of the pharmaceutical composition;
(5) a content of benzyl alcohol is 5% by mass to 24% by mass with respect to the entire mass of the pharmaceutical composition; and
(6) a content of benzyl benzoate is 8% by mass to 19% by mass with respect to the entire mass of the pharmaceutical composition.

2. The pharmaceutical composition according to claim 1, wherein the content of ethanol is less than 0.5% by mass with respect to the entire mass of the pharmaceutical composition.

3. The pharmaceutical composition according to claim 1, wherein a content of propylene glycol is 12% by mass to 18% by mass with respect to the entire mass of the pharmaceutical composition.

4. The pharmaceutical composition according to claim 1, wherein the content of benzyl alcohol is 5% by mass to 15% by mass with respect to the entire mass of the pharmaceutical composition.

5. The pharmaceutical composition according to claim 1, wherein the content of benzyl benzoate is 10% by mass to 16% by mass with respect to the entire mass of the pharmaceutical composition.

6. A pharmaceutical composition comprising:
fulvestrant;
propylene glycol;
benzyl alcohol;
benzyl benzoate; and
castor oil,
wherein the pharmaceutical composition satisfies the following requirements (i) to (vi);
(i) a content of ethanol is less than 0.5% by mass with respect to the entire mass of the pharmaceutical composition;
(ii) a content of benzoic acid is less than 1% by mass with respect to the entire mass of the pharmaceutical composition;
(iii) a content of fulvestrant is 4.5% by mass to 10.0% by mass with respect to the entire mass of the pharmaceutical composition;
(iv) a content of propylene glycol is 12% by mass to 18% by mass with respect to the entire mass of the pharmaceutical composition;
(v) a content of benzyl alcohol is 5% by mass to 15% by mass with respect to the entire mass of the pharmaceutical composition; and
(vi) a content of benzyl benzoate is 10% by mass to 16% by mass with respect to the entire mass of the pharmaceutical composition.

7. The pharmaceutical composition according to claim 1, which is for intramuscular injection.

8. The pharmaceutical composition according to claim 6, which is for intramuscular injection.

9. The pharmaceutical composition according to claim 1, wherein a content of castor oil is equal to or greater than 40% by mass with respect to the entire mass of the pharmaceutical composition.

10. The pharmaceutical composition according to claim 1, wherein a content of castor oil is equal to or greater than 55% by mass with respect to the entire mass of the pharmaceutical composition.

11. The pharmaceutical composition according to claim 1, wherein a content of castor oil is equal to or less than 70% by mass with respect to the entire mass of the pharmaceutical composition.

* * * * *